US 6,527,701 B1

(12) United States Patent
Sayet et al.

(10) Patent No.: US 6,527,701 B1
(45) Date of Patent: Mar. 4, 2003

(54) BODY FLUID FLOW CONTROL DEVICE (75) Inventors: Peter H. Sayet, Fort Lauderdale, FL (US); Lloyd A. Sutherland, Boca Raton, FL (US); Victor A. Politano, North Miami, FL (US)

(73) Assignee: Precision Medical Devices, Inc., Fort Lauderdale, FL (US)

( * ) Notice: Subject to any disclaimer, the term of this patent is extended or adjusted under 35 U.S.C. 154(b) by 0 days.

(21) Appl. No.: 09/676,336

(22) Filed: Sep. 29, 2000

(51) Int. Cl.$^7$ .................................................. A61F 2/02
(52) U.S. Cl. ........................................................ 600/30
(58) Field of Search ............... 600/29–37; 128/DIG. 25

(56) References Cited

U.S. PATENT DOCUMENTS

| | | | | |
|---|---|---|---|---|
| 3,419,008 A | * | 12/1968 | Plishner | 600/31 |
| 3,815,576 A | * | 6/1974 | Balaban | 600/30 |
| 3,854,469 A | * | 12/1974 | Giori et al. | 128/DIG. 25 X |
| 3,924,631 A | * | 12/1975 | Mancusi et al. | 600/30 |
| 3,926,175 A | * | 12/1975 | Allen et al. | 600/30 |
| 4,024,855 A | * | 5/1977 | Bucalo | 600/30 |
| 4,258,705 A | * | 3/1981 | Sorensen et al. | 600/30 |
| 4,643,169 A | * | 2/1987 | Koss et al. | 128/DIG. 25 X |
| 4,800,900 A | * | 1/1989 | French | 128/DIG. 25 X |
| 4,994,019 A | * | 2/1991 | Fernandez et al. | 600/30 |
| 4,994,020 A | * | 2/1991 | Polyak | 600/31 |
| 5,163,897 A | * | 11/1992 | Persky | 600/31 |
| 5,509,888 A | * | 4/1996 | Miller | 600/29 |
| 5,562,598 A | * | 10/1996 | Whalen et al. | 600/29 |
| 6,095,969 A | * | 8/2000 | Karram et al. | 600/31 |
| 6,135,945 A | * | 10/2000 | Sultan | 600/30 |
| 6,210,347 B1 | * | 4/2001 | Forsell | 600/3 X |

* cited by examiner

Primary Examiner—Kevin Shaver
Assistant Examiner—Joseph A. Cadugan
(74) Attorney, Agent, or Firm—Akerman Senterfitt (57) ABSTRACT

An implantable apparatus for controlling fluid flow within a host body includes a constricting member with a plunging member for reducing fluid flow within a body canal when in a closed position. A biasing member biases the constricting member against the body canal. A pulling member counters the force exerted by the biasing member such that when activated, the constricting member is forced away from the closed position so as to allow increased fluid flow within the body canal. An activating member activates the pulling member.

42 Claims, 8 Drawing Sheets

FIG. 11b

BODY FLUID FLOW CONTROL DEVICE

U.S. PATENT APPLICATION

This application for U.S. patent is filed as an application under U.S.C., Title 35 §111(a).

FIELD OF THE INVENTION

The invention relates to implantable medical devices for the control of fluid flow through a body host canal or vessel, such as an urethra.

BACKGROUND

Incontinence is a condition wherein persons lose control over their voluntary, urinary function. The condition can arise from various causes. These causes include a variety of related and unrelated diseases, aging, and deterioration of the voluntary urethra sphincter muscle. The cost and inconvenience to persons suffering from this condition are great. Several remedies exist that are known in the prior art. Among these, the most common are surgical corrections (minor and major), drugs, and devices which serve to capture discharges (i.e., "capture" or diaper systems). Another solution is to place a patch over the urinary orifice to prevent unwanted discharge. Possibly, the most effective solution to date is the use of artificial sphincters. These devices are surgically installed and are hydraulically or pneumatically driven, operating by inflation of ballasts to suppress fluid flow. However, control of these devices is not always easy and is often inconvenient. Accordingly, there is a need for an improved method and apparatus to control the urinary function.

SUMMARY OF THE INVENTION

The present invention overcomes and alleviates the above-mentioned drawbacks and disadvantages in the art through the discovery of novel implantable body fluid flow control devices for the control of fluid flow through a host body canal or vessels, such as an urethra.

Generally speaking, and in accordance with the invention, an implantable apparatus for controlling fluid flow within a host body comprises (1) a constricting member for reducing fluid flow within a body canal when in a closed position, (2) a biasing member for biasing the constricting member against the body canal, (3) a pulling member for countering the force exerted by the biasing member such that when activated the constricting member is forced away from the closed position so as to allow increased fluid flow within the body canal, and (4) an activating member for activating the pulling member.

The object and advantages of the implantable fluid flow control devices of the present invention permit implantation and use without severing the canal or vessel to be constricted. Moreover, because trauma is minimized with respect to the canal or vessel, and the devices of the present invention are relatively small, lightweight and made of corrosion-resistant material, such as durable plastics or stainless steel, the devices are suitable for use for extended period of time to control fluid flow through numerous types of vessels to control, for example, urination, ejaculation, nutrition absorption, obesity, etc.

These and other objects, features and advantages of the present invention may be better understood and appreciated from the following detailed description of the embodiments thereof, selected for purposes of illustration and shown in the accompany Figs. It should therefore be understood that the particular embodiments illustrating the present invention are exemplary only and not to be regarded as limitations of the present invention.

BRIEF DESCRIPTION OF THE FIGS.

The foregoing and, other objects, advantages and features of the present invention, and the manner in which the same are accomplished, will become more readily apparent upon consideration of the following detailed description of the present invention taken in conjunction with the accompany FIGS. which illustrate preferred and exemplary embodiments, and wherein.

DETAILED DESCRIPTION OF THE INVENTION

By way of illustrating and providing a more complete appreciation of the present invention and many of the attendant advantages thereof, the following detailed description is given concerning the novel implantable body fluid control devices and uses thereof.

Referring now in more detail to the FIGS., in which like numerals refer to like parts throughout several views, FIGS.

Figure 1:
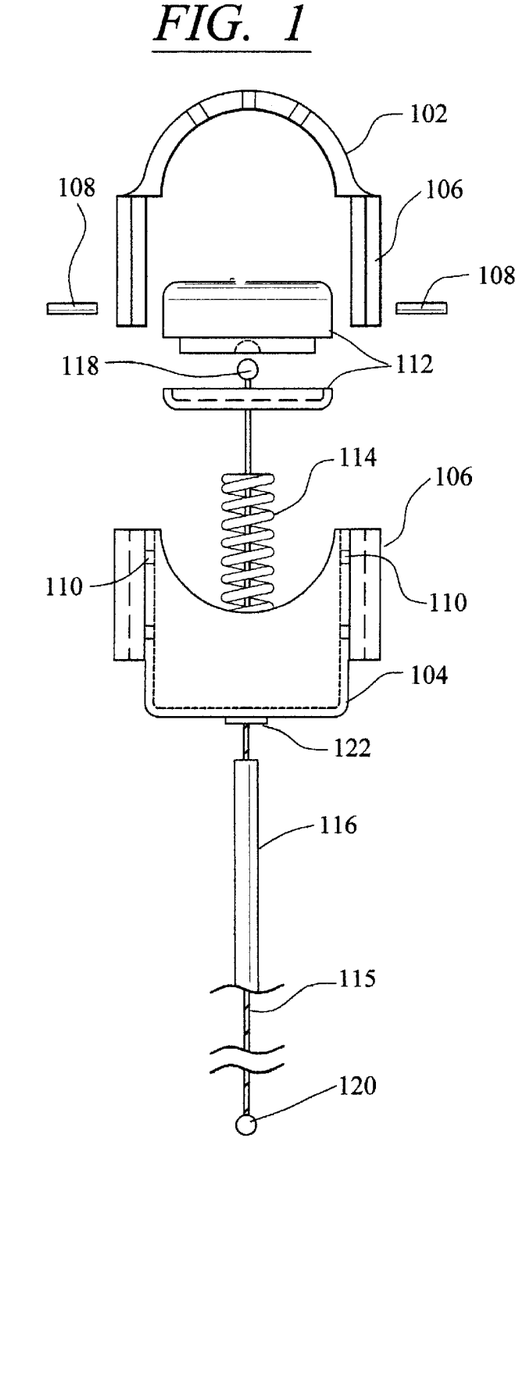
FIG. 1 is a first partial side explosion view of a body fluid control device according to the invention.
Figure 2:
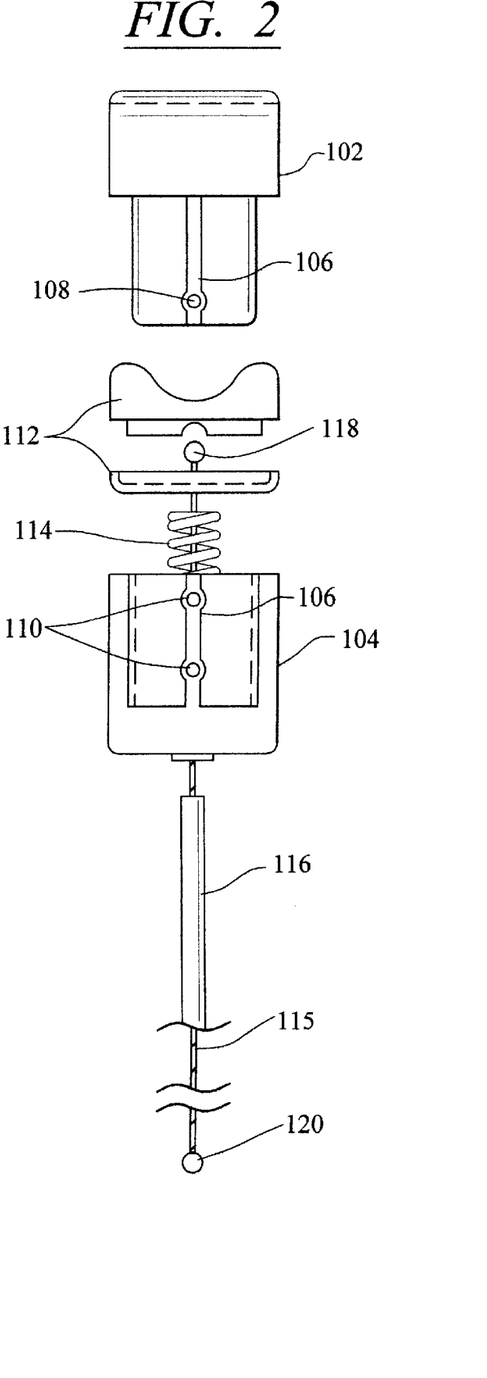
FIG. 2 is a second partial side explosion view of the body fluid control device.
Figure 3A:
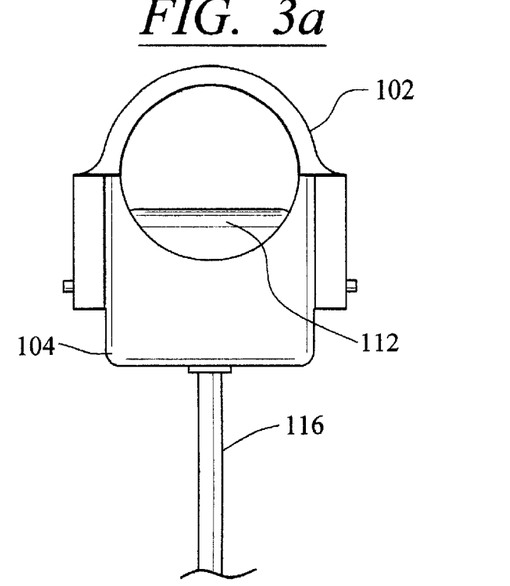
FIG. 3(a) is a partial side view of the device shown in FIG. I in the closed position.
Figure 3B:
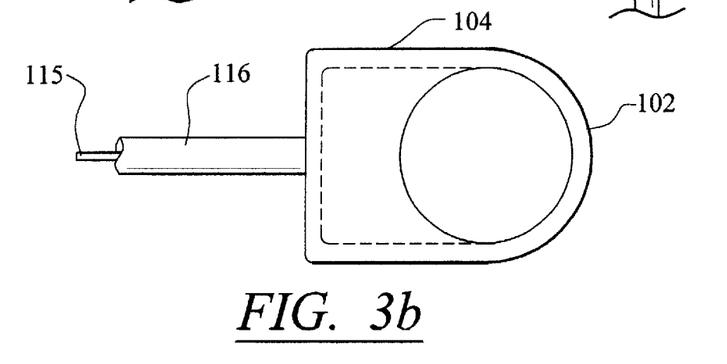
FIG. 3(b) is a partial view of an alternative device depicted in FIG. 3(a).
Figure 4A:
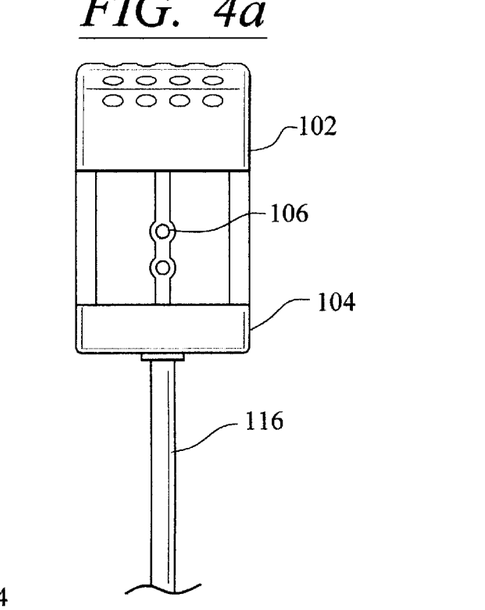
FIG. 4(a) is a partial side view of the device shown in FIG. 2 in the closed.
Figure 4B:
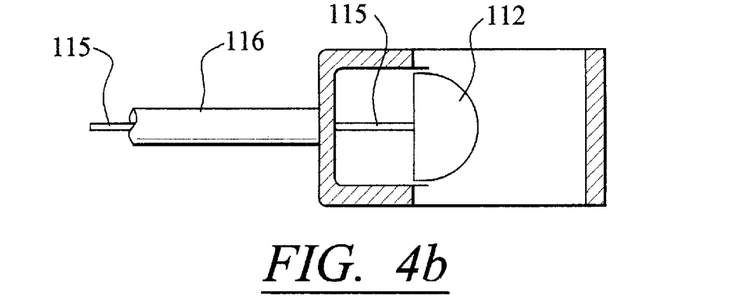
FIG. 4(b) is a partial side view of an alternative device.

1 and 2 show partial side explosion views of a body fluid flow control device according to the present invention. In one embodiment, the body fluid flow control device comprises a first engaging element 102 and a second engaging element 104. When the first engaging element 102 is coupled with the second engaging element 104, an inner diameter is formed which is well suited for fitting around a host body canal, i.e., any tube or vessel within the human or other animal body, such as the urethra. The body fluid flow control device also comprises a locking mechanism 106 for locking the first and second engaging elements 102 and 104 together. The locking mechanism 106 as shown is in the form of locking pins 108 located on the first engaging element 102 and locking holes 110 located on the second engaging element 104. It should be understood that any other equivalent locking mechanism can be used for this purpose. Alternative locking mechanisms contemplated by the present invention include, but are not limited to, the use of a strap and snap pins or interconnecting molding on the first and second engaging elements 102 and 104. The body fluid flow control devices of the present invention further includes a plunging member 112 located within the inner diameter formed by the coupling of the first and second engaging elements 102 and 104 such that the plunging member 112 applies pressure against a body canal or vessel, such as an urethra.

A biasing member is utilized by the body fluid flow control device of the present invention so as to force the plunging member 112 to normally apply pressure against the body canal when the body fluid flow control device is in the closed position. The biasing member, in on embodiment, comprises at least one spring 114 situated between the plunging member 112 and the second engaging element 104. Alternative biasing members include the use of any structural support which, when in the normal position, will force the plunging member 112 away from the second engaging element 104 and towards the body canal and which may be offset by the pulling member described below.

A pulling member is utilized to offset the force of the biasing member when the body fluid flow control device of the present invention is activated. The pulling member comprises a cable 115 covered by a protective sleeve 116 with a first end 118 and a second end 120.The first end 118 of the cable 115 runs slidably through the second engaging element 104 and is attached to the plunging member 112. FIGS. 3(a) and 3(b) and FIGS. 4(a) and 4(b) show the above described portion of the invention in the closed position.

Figure 5A:
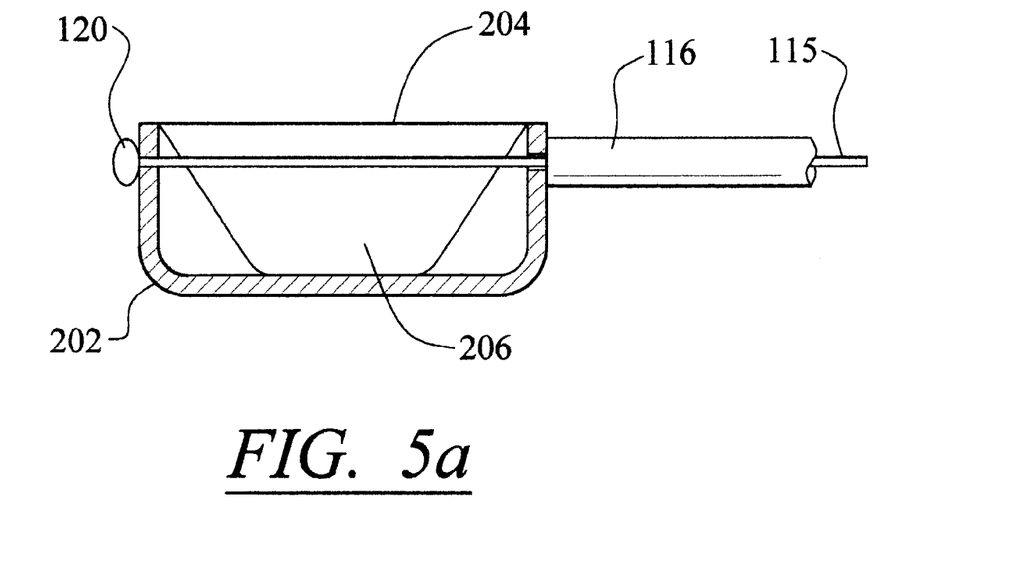
FIG. 5(a) is a side-sectional view of a manual activating member.
Figure 5B:
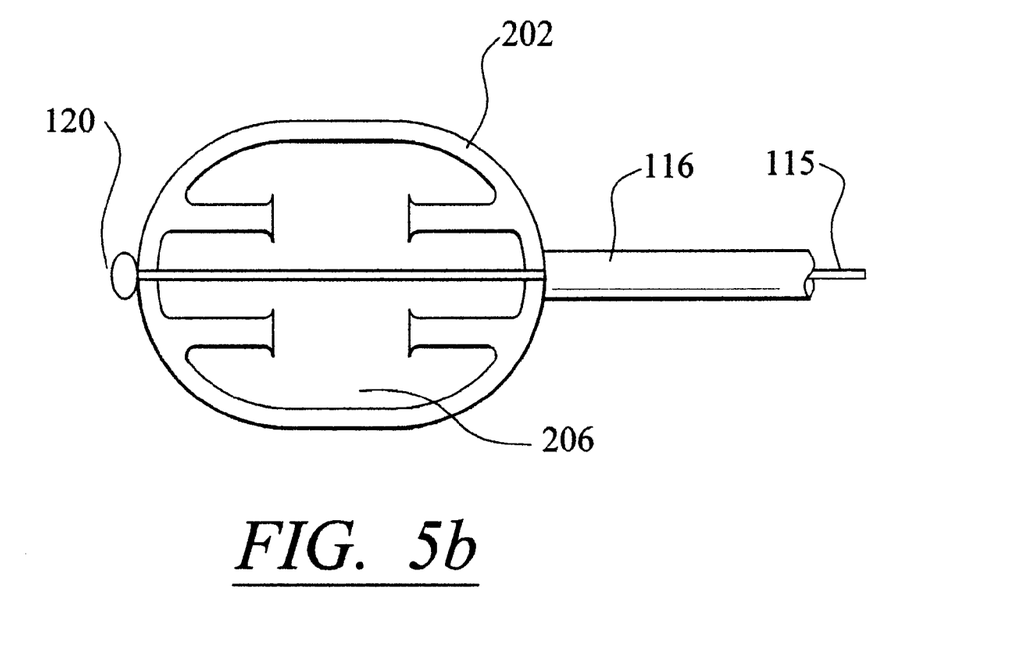
FIG. 5(b) is a top view of the manual activating member shown in FIG. 5(a).

FIGS. 5(a) and 5(b) illustrate an activating member comprising a housing 202, a thin silicone membrane 204, and a cup 206 for facilitating the storage of the expanse of cable 115 placed therein during activation of the body fluid flow control device. The second end 120 of the cable 115 runs slidably through a side of the housing 202 and is fixed to the opposite side of the housing 202. The activating member is placed such that substantially perpendicular pressure against the portion of cable 115 running between the two sides of the housing 202 results in movement of the plunging member 112 away from the body canal allowing at least some fluid flow there through. The placement of substantially perpendicular pressure against the housed cabling results in movement of the first end 118 of the cable 115 offsetting the force exerted by the biasing member 114 against the plunging member 112.

Figure 6A:
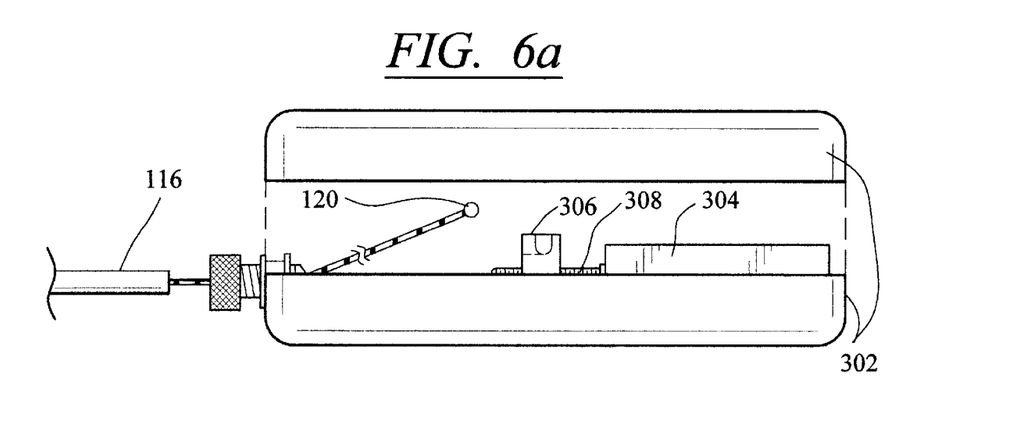
FIG. 6(a) is a side sectional view of a motorized activating member.
Figure 6B:
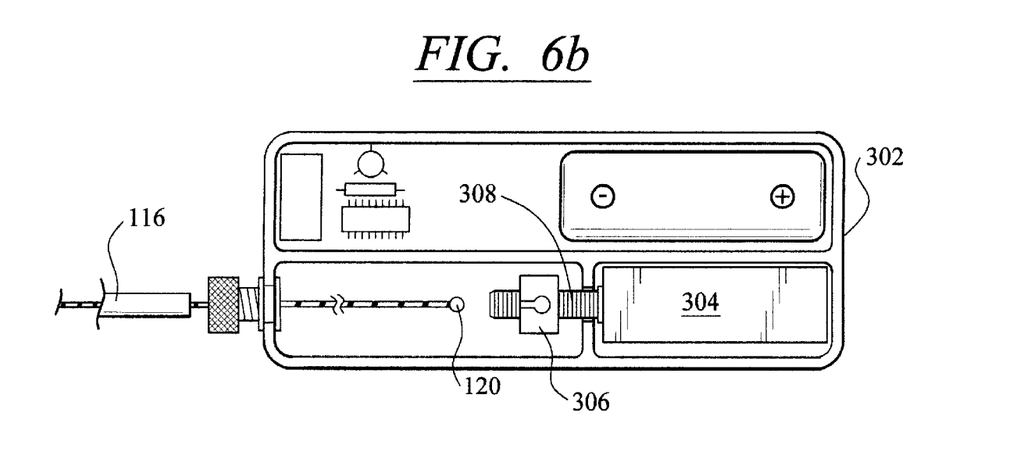
FIG. 6(b) is a top view of the motorized activating member shown in FIG. 6(a).

FIGS. 6(a) and 6(b) illustrate an alternative activating member contemplated by the present invention. This alternative activating member comprises a housing 302, a stepper motor 304, a cable mounting block 306, and a threaded shaft 308 attached to the stepper motor. The second end of the cable 120 runs slidably through a first side of the housing 302 and is fixed to the cable mounting block 304. The stepper motor 304 is mounted on the opposite side of the housing 302. The block 306 is mounted on the threaded shaft 308 such that activation of the motor 304 turns the shaft 308 and the block 304 is axially pulled towards the motor. The activating member is placed such that movement of the block 306 results in movement of the plunging member 112 away from the body canal allowing at least some fluid flow there through. The movement of the block 306 results in movement of the first end 118 of the cable 115 offsetting the force exerted by the biasing member 114 against the plunging member 112.

Figure 7A:
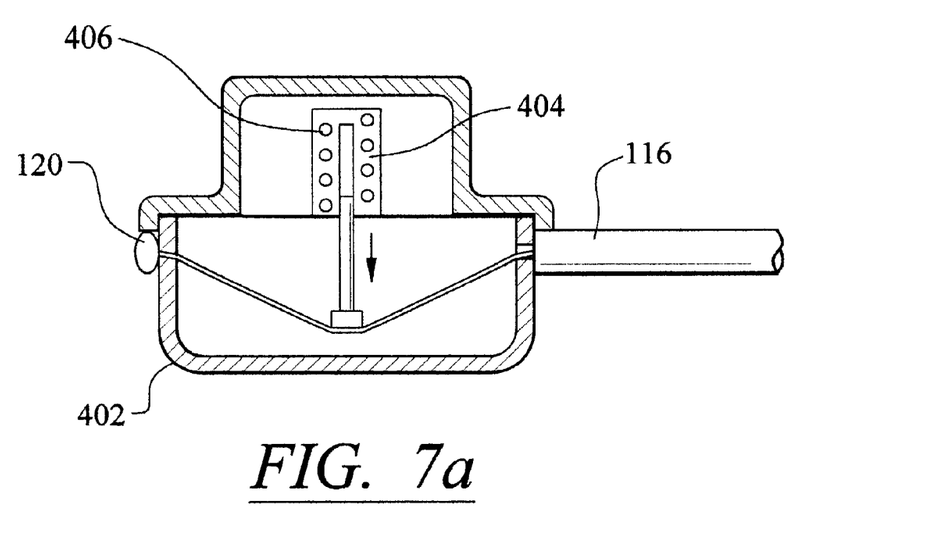
FIG. 7(a) is side sectional view of a solenoid activating member.
Figure 7B:
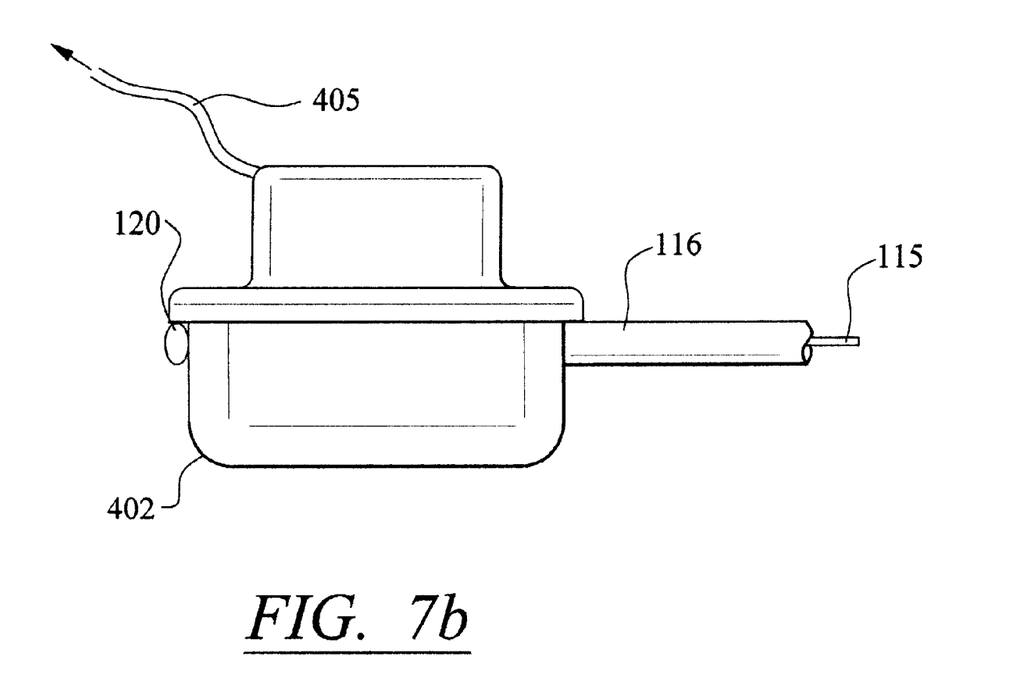
FIG. 7(b) is a side sectional view of the member shown in FIG. 7(a).

FIGS. 7(a) and 7(b) illustrate yet another activating member contemplated by the present invention. The activating member comprises a housing 402 and a piston-like solenoid mechanism 404 having wratchet holes 406 for connection to a manual switch via wire 405. The second end 120 of the cable 115 runs slidably through a side of the housing 402 and is fixed to the opposite side of the housing 402. Activation of the solenoid 404 causing a piston to move downwards against the portion of cable 115 running between the two sides of the housing 402. The activating member is placed such that the application of this substantially perpendicular pressure against the housed cabling results in movement of the first end of the cable 115 offsetting the force exerted by the biasing member 114 against the plunging member 112. This results in movement of the plunging member 112 away from the body canal allowing at least some fluid flow there through.

Figure 11A:
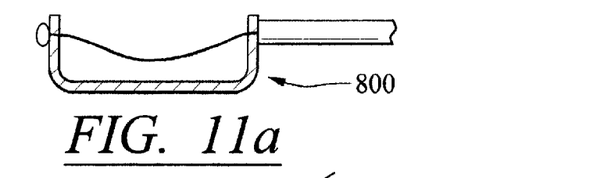
FIG. 11(a) is a partial side view of a manual switch for use with the device of the present invention.
Figure 11B:
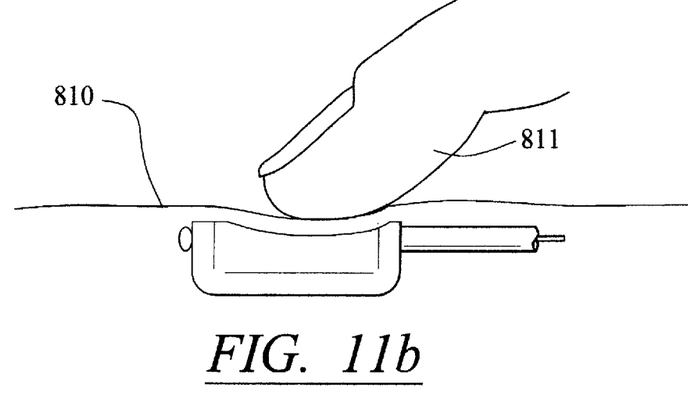
FIG. 11(b) is a partial side view of the manual switch depicted in FIG. 11(b) but shown implanted under skin and being activated by a user of a device of the present invention.

The body fluid flow control devices of the present invention may utilize a number of triggering mechanism options, such as a touch sensor as shown FIGS. 11(a) and 11(b), infrared, voice or sound activation. Any of the several well-known control devices can be used to control the operation of the body fluid flow control devices of the present invention by a user so long as the objectives of the present invention are not defeated.

As discussed above, the body fluid flow control devices of the present invention are surgically implanted into a human or other animal host. In addition to implanting a body fluid flow control device of the present invention, the host will require a control mechanism that can be operated by the host from outside the host. One simple example as depicted in FIGS. 11(a) and 11(b) is a switch 800 implanted just underneath the host's skin 810 such that the host can activate it by pressing with a finger 811 on the skin above the switch. Any of several known pressure-activated switches will do provided that they are made from a suitable corrosion resistant material. Another control mechanism could be a smart card having a coil or other member for generating electromagnetic signals that control a control device inside the host.

Figure 8:
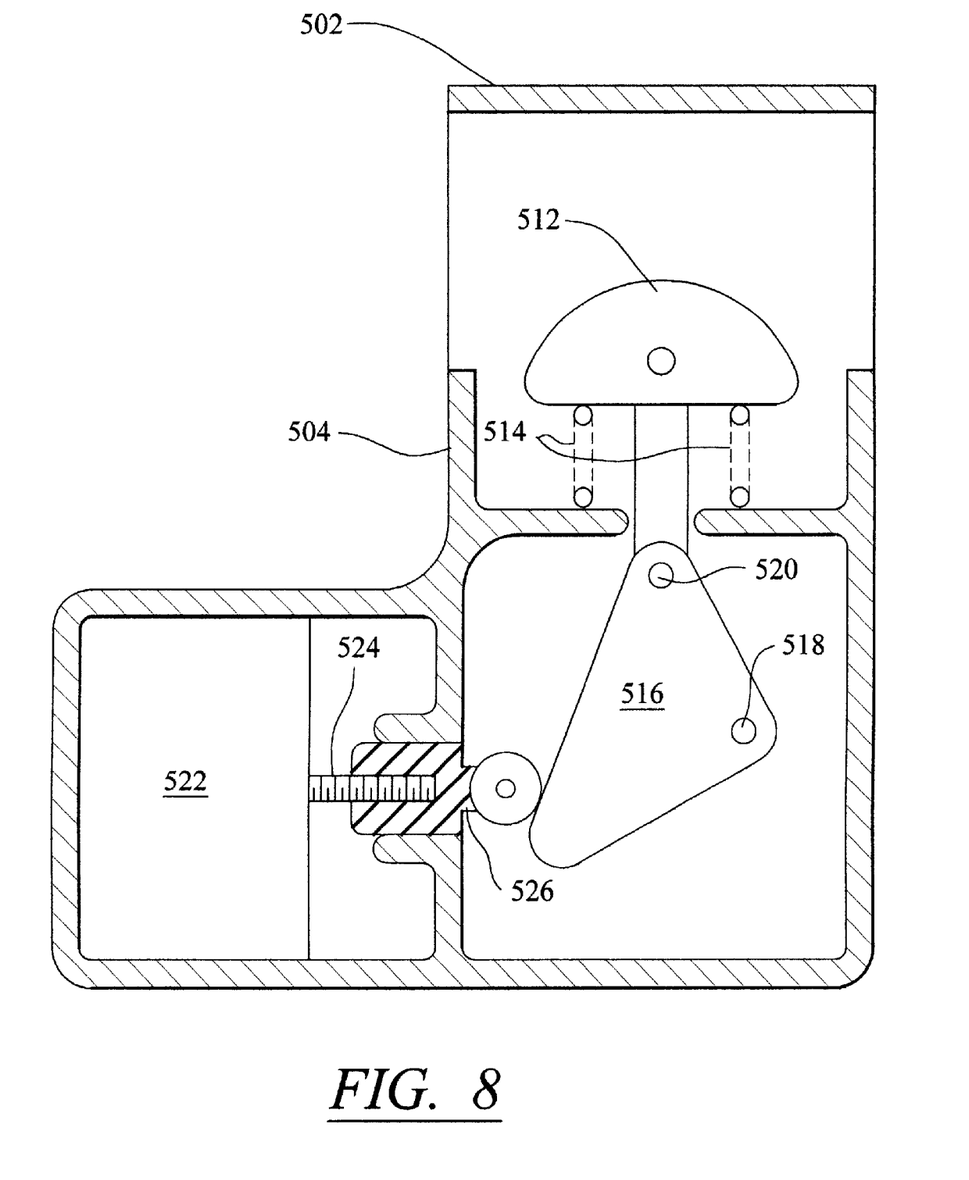
FIG. 8 is a side sectional view of an alternative embodiment of a body fluid flow control device according to the invention.

FIG. 8 illustrates another alternative embodiment of the present invention. Similar to the embodiment referred to in FIGS. 1 and 2, the body fluid flow control device comprises a first engaging element 502, a second engaging element 504, a locking mechanism (not shown) for locking the first and second engaging elements 502 and 504 together, a plunging member 512 located within the inner diameter formed by the coupling of the first and second engaging elements 502 and 504, and a biasing member 514 so as to force the plunging member 512 to normally apply pressure against the body canal when the device is in the closed position.

A pulling member is utilized to offset the force of the biasing member when the body fluid flow control device is activated. The pulling member comprises a triangular shaped pivot member 516 with three corners wherein the first corner opposite the hypotenuse has a fixed pivot point 518 and the second corner has a floating pivot point 520 coupled to the plunging member 512. The body fluid flow control device further comprises a stepper motor 522, a threaded shaft 524, and a bearing wheel assembly 526. The bearing wheel assembly 526 is mounted on the threaded shaft 524 such that activation of the motor 522 turns the shaft 524 and the bearing wheel 526 moves away from the motor 522 and against the triangular pivot member 516. The force exerted by the bearing wheel 526 against the triangular pivot member 516 forces the pivot member 516 to move along its fixed pivot 518. Movement of the pivot member 516 along its fixed pivot point 518 causes the floating pivot point 520 to move in a downward motion offsetting the force exerted by the biasing member 514 against the plunging member 512. This results in movement of the plunging member 512 away from the body canal allowing at least some fluid flow there through.

Figure 9A:
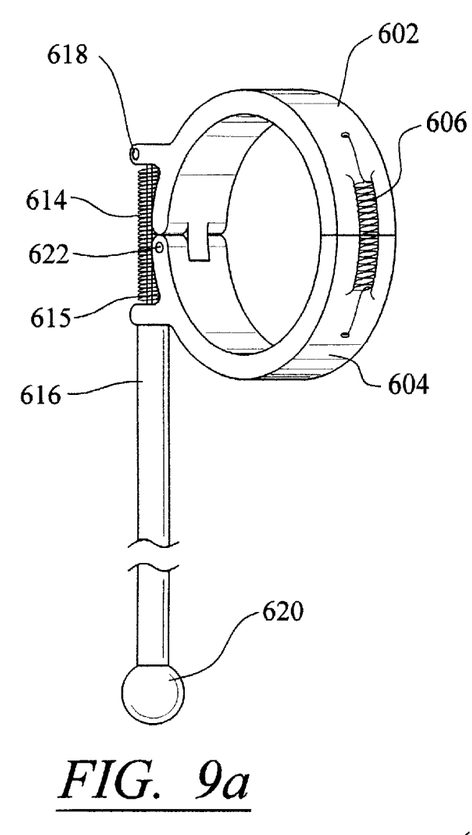
FIG. 9(a) is a partial side view of another alternative embodiment of the invention in the closed position.
Figure 9B:
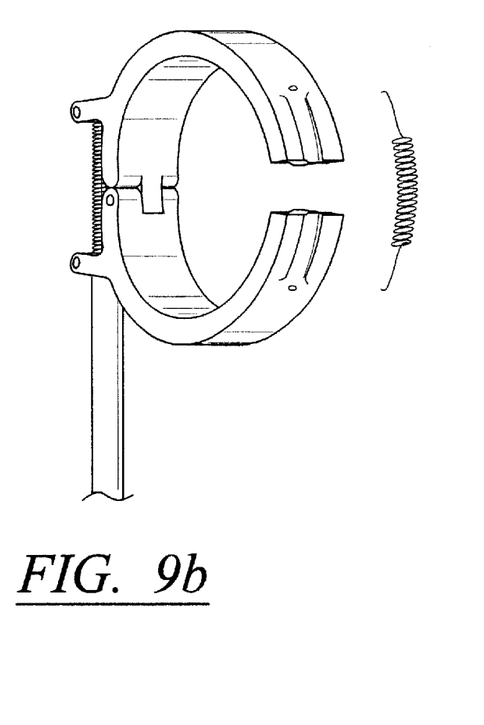
FIG. 9(b) is a partial side view of the alternative embodiment shown in FIG. 9(a).
Figure 9C:
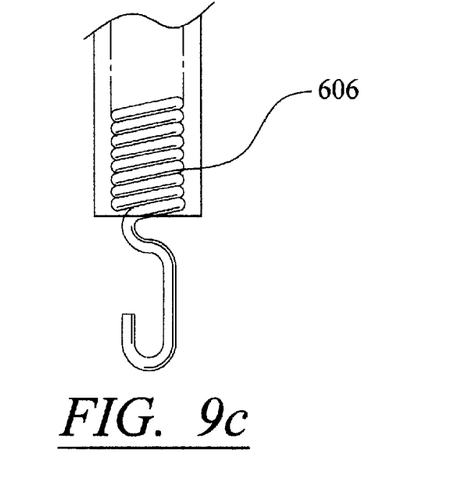
FIG. 9(c) is an exploded view of a section of the alternative embodiment depicted in FIG. 9(a).

FIG. 9 illustrates another embodiment of the present invention. Similar to the embodiment referred to in FIGS. 1 and 2, the body fluid flow control device comprises a first engaging element 602, a second engaging element 604, a flexible locking mechanism 606 for locking the first and second engaging elements 602 and 604 together, a biasing member 614, and a cable 615 within a protective sleeve 616 with a first end 618 and a second end 620. The first engaging element 602 and second engaging element 604 are hinged together on a fixed pivot point 622. The biasing member 614 is situated behind the pivot point 622 such that it forces the first engaging element 602 and second engaging elements 604 into a closed position. The closure of the engaging elements 602 and 604 constricts the body canal situated between them. A flexible locking mechanism 606, such as a spring, is utilized to maintain the engaging elements 602 and 604 in a normally closed position. The first end 618 of the cable 615 runs slidably through the second engaging element 604, running parallel with the biasing member 614, and is fixed to the first engaging element 604.

The activating member described in reference to FIGS. 5, 6 and 7 are equally applicable with this embodiment of the present invention. Rather than affecting the positioning of a plunging member, activation of the body fluid flow control device in this embodiment results in the first end 618 of the cable 615 moving against the force exerted by the biasing member 614 causing the first engaging element 602 to move along the pivot point 622 therefore opening the inner diameter of the body fluid flow control device allowing at least some fluid flow there through.

Figure 10A:
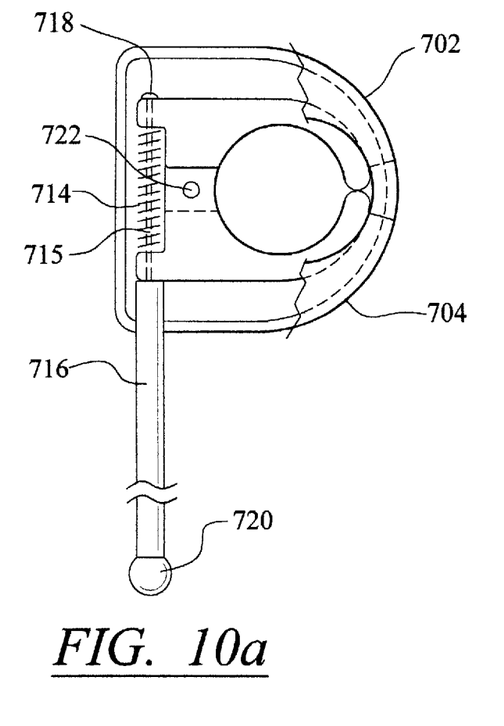
FIG. 10(a) is a partial side view of yet another alternative embodiment of the invention in the closed position.
Figure 10B:
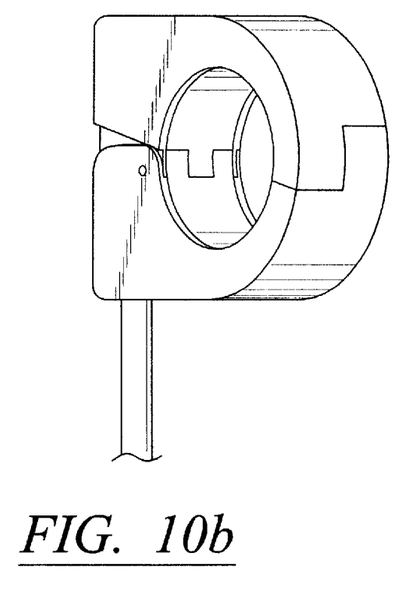
FIG. 10(b) is a partial side view of the alternative embodiment shown in FIG. 10(a).

FIG. 10 illustrates yet another embodiment contemplated by the present invention similar to the embodiment described in reference to FIG. 9 but without the flexible locking mechanism. As with the prior embodiment, this embodiment comprises a first engaging element 702, a second engaging element 704, a biasing member 714, a cable 715 covered with a protective sleeve 716 with a first end 718 and a second end 720, and a pivot point 722. This embodiment operates in the same manner as previously described regarding the prior embodiment as described with reference to FIG. 9.

Accordingly, it will be understood that various embodiments of the present invention have been disclosed by way of example and that other modifications and alterations may occur to those skilled in the art without departing from the scope and spirit of the appended claims. Thus, the invention described herein extends to all such modifications and variations as will be apparent to the reader skilled in the art, and also extends to combinations and subcombinations of the features of this description and the accompanying FIGS. Although preferred embodiments of the present invention have been illustrated in the accompanying FIGS. and described in the foregoing detailed description, it will be understood that the present invention is not limited the embodiments disclosed, but is capable of numerous rearrangements, modifications and substitutions without departing from the spirit of the present invention as set forth and defined by the following claims, such as for example those embodiments described in non-provisional U.S. patent application, Ser. No. 09/048,823, filed Mar. 26, 1998, which is incorporated hereinto in its entirety by reference.

Having described our invention, we claim:

1. An implantable apparatus for controlling fluid flow within a host body comprising:
    a constricting member for reducing fluid flow within a body canal when in a closed position, said constricting member comprising a plunging member for applying pressure against the body canal;
    a biasing member for biasing said plunging member against the body canal;
    a pulling member for countering the force exerted by said biasing member such that when activated said plunging member is forced away from the closed position so as to allow increased fluid flow within the body canal, said pulling member being mechanically connected to said plunging member; and
    an activating member for activating said pulling member.

2. An implantable apparatus of claim 1 wherein said constricting member comprises a first engaging element and a second engaging element for coupling to the first engaging element to encircle a body canal.

3. An implantable apparatus of claim 2 further comprising a locking member for locking the first engaging element and second engaging element into a locked position.

4. An implantable apparatus of claim 2 further comprising a plunging member located within the first engaging element and the second engaging element such that the plunging member may apply pressure against the body canal.

5. An implantable apparatus of claim 4 wherein said biasing member comprises at least one spring situated between said plunging member and the second engaging element such that said plunging member will normally apply pressure against the body canal.

6. An implantable apparatus of claim 4 wherein said pulling member comprises a cable having at least a first and second end.

7. An implantable apparatus of claim 6 wherein the first end of the cable is running slidably through the second engaging element and is attached to said plunging member.

8. An implantable apparatus of claim 6 wherein said activating member comprises a housing having at least a first side and a second side whereby the second end of the cable is running slidably through the first side of the housing and is fixed to the second side of the housing such that substantially perpendicular pressure against a portion of cable between the first side and the second side of the housing results in movement of said plunging member away from the body canal to allow at least some fluid flow there through.

9. An implantable apparatus of claim 6 wherein said activating member comprises a stepper motor coupled to the second end of the cable so that activation of the stepper motor causes the second end of the cable to be axially pulled towards the stepper motor resulting in movement of said plunging member away from the body canal to allow at least some fluid flow there through.

10. An implantable apparatus of claim 9 further comprising a magnet for activating the stepper motor.

11. An implantable apparatus of claim 6 wherein said activating member comprise
   a housing having at least a first side and second side whereby the second end of the cable is running slidably through the first side of the housing and is fixed to the second side of the housing, and
   a solenoid such that activation of the solenoid results in downward force being exerted against a portion of the cable between the first side and the second side of the housing thereby causing movement of said plunging member away from the body canal to allow at least some fluid flow there through.

12. An implantable apparatus of claim 11 further comprising a magnet for activating the solenoid.

13. An implantable apparatus of claim 1 wherein said constricting member comprises a first shell and a second shell pivotally connected such that the second shell is movable from an open position to a closed position.

14. An implantable apparatus of claim 13 whereby the movement of the second shell to a closed position constricts the body canal thus reducing fluid flow within the body canal.

15. An implantable apparatus of claim 13 wherein said biasing member comprises at least one spring exerting outward force approximate to the pivot point of said constricting member forcing said constricting member to be in a normally closed position such that said constricting member constricts the body canal.

16. An implantable apparatus of claim 13 wherein said pulling member comprises a cable having at least a first end and a second end.

17. An implantable apparatus of claim 16 whereby the first end of the cable is running slidably through the first shell of said constricting member running parallel to said biasing member and is attached to the second shell of said constricting member.

18. An implantable apparatus of claim 16 wherein said activating member comprises a housing having at least a first side and a second side whereby the second end of the cable is running sidably through the first side of the housing and is fixed to the second side of the housing such that substantially perpendicular pressure against a portion of the cable between the first side and the second side of the housing results in movement of the first end of the cable against the force exerted by said biasing member causing said constricting member to move away from the closed position to allow at least some fluid flow through the body canal.

19. An implantable apparatus of claim 16 wherein said activating member comprises a stepper motor coupled to the second end of the cable so that activation of the stepper motor causes the second end of the cable to be axially pulled towards the stepper motor resulting in movement of said plunging member away from the body canal to allow at least some fluid flow there through.

20. An implantable apparatus of claim 19 further comprising a magnet for activating the stepper motor.

21. An implantable apparatus of claim 16 wherein said activating member comprises
   a housing having at least a first side and second side whereby the second end of the cable is running slidably through the first side of the housing and is fixed to the second side of the housing, and
   a solenoid such that activation of the solenoid results in downward force being exerted against a portion of the cable between the first side and the second side of the housing thereby causing movement of the first end of the cable against the force exerted by said biasing member causing the constricting member to move away from the closed position to allow at least some fluid flow through the body canal.

22. An implantable apparatus of claim 21 further comprising a magnet for activating the solenoid.

23. An implantable apparatus for controlling fluid flow within a host body comprising:
   a constricting member for reducing fluid flow within a body canal when in a closed position, said constricting member comprising a first engaging element and a second engaging element for coupling to the first engaging element to encircle a body canal, and further comprising a plunging member located within the first engaging element and the second engaging element such that the plunging member may apply pressure against the body canal;
   a biasing member for biasing said constricting member against the body canal;
   a pulling member for countering the force exerted by said biasing member such that when activated said constricting member is forced away from the closed position so as to allow increased fluid flow within the body canal;
   said pulling member further comprising a triangular shaped pivot member with three corners wherein the first corner opposite the hypotenuse is a fixed pivot point and the second corner is a floating pivot point coupled to said plunging member so that movement on the fixed pivot point results in movement of said plunging member away from the body canal to allow at least some fluid flow there through; and
   an activating member for activating said pulling member.

24. An implantable apparatus of claim 23 wherein said activating member comprises a stepper motor coupled to a bearing wheel so that activation of the stepper motor moves the bearing wheel so as to force the triangular shaped pivot member to move along its fixed pivot point such that the floating pivot point coupled to said plunging member moves so as to pull said plunging member away from the body canal to allow at least some fluid flow there through.

25. An implantable apparatus of claim 24 further comprising a magnet for activating the stepper motor.

26. An implantable apparatus for controlling fluid flow within a host body comprising:
   an engaging housing comprising a first engaging element and second engaging element for coupling to the first engaging element to encircle a body canal;
   a plunging member situated within said engaging housing which will apply pressure against the body canal;
   a biasing member for biasing said plunging member against the body canal such that said plunging member will normally apply pressure against the body canal;
   a cable with a first and second end whereby the first end is running slidably through said engaging housing and is attached to said plunging member; and
   an activating member mechanically connected to said second end of said cable for activating said implantable apparatus such that said plunging member moves away from the body canal to allow at least some fluid flow there through.

27. An implantable apparatus of claim 26 wherein said biasing member comprises at least one spring situated between said plunging member and said engaging housing.

28. An implantable apparatus of claim 26 wherein said activating member comprises a control housing having at least a first and second side whereby the second end of the cable is running slidably through the first side of the control housing and is fixed to the second side of the control housing such that substantially perpendicular pressure against a portion of the cable between the first side and the second side of the control housing results in movement of the plunging member away from the body canal to allow at least some fluid flow there through.

29. An implantable apparatus of claim 26 wherein said activating member comprises a stepper motor coupled to the second end of the cable so that activation of the stepper motor causes the second end of the cable to be axially pulled towards the stepper motor resulting in movement of said plunging member away from the body canal to allow at least some fluid flow there through.

30. An implantable apparatus of claim 29 further comprising a magnet for activating the stepper motor.

31. An implantable apparatus of claim 26 wherein said activating member comprises
  a housing having at least a first side and second side whereby the second end of the cable is running slidably through the first side of the housing and is fixed to the second side of the housing, and
  a solenoid such that activation of the solenoid results in downward force being exerted against a portion of the cable between the first side and the second side of the housing thereby causing movement of said plunging member away from the body canal to allow at least some fluid flow there through.

32. An implantable apparatus of claim 31 further comprising a magnet for activating the stepper motor.

33. An implantable apparatus for controlling fluid flow within a host body comprising:
  an engaging housing comprising a first engaging element and second engaging element for coupling to the first engaging element to encircle a body canal;
  a plunging member situated within said engaging housing which will apply pressure against the body canal;
  a biasing member for biasing said plunging member against the body canal such that said plunging member will normally apply pressure against the body canal;
  a triangular shaped pivot member with three corners wherein the first corner opposite the hypotenuse is a fixed pivot point and the second corner is a floating pivot point coupled to said plunging member; and
  a stepper motor coupled to a bearing wheel so that activation of the stepper motor moves the bearing wheel so as to force the triangular shaped pivot member to move along its fixed pivot point such that the floating pivot point coupled to said plunging member moves so as to pull the plunging member away from the body canal to allow at least some fluid flow there through.

34. An implantable apparatus of claim 33 wherein said biasing member comprises at least one spring situated between said plunging member and said engaging housing.

35. An implantable apparatus of claim 33 further comprising a magnet for activating the stepper motor.

36. An implantable apparatus for controlling fluid flow within a host body comprising:
  a first shell and a second shell pivotally connected such that said second shell is movable from an open position to a closed position whereby movement of said second shell to a closed position constricts a body canal thus reducing fluid flow;
  a biasing member for biasing said first shell and said second shell around the body canal such that said second shell will normally apply pressure against the body canal;
  a cable with a first end and a second end whereby the first end of said cable is running slidably through said first shell running parallel to said biasing member and is attached to said second shell; and
  an activating member mechanically connected to said second end of said cable for activating said implantable apparatus such that said second shell moves away from the body canal to allow at least some fluid flow there through.

37. An implantable apparatus of claim 36 wherein said biasing member comprises at least one spring exerting outward force approximate to the pivot point of said first shell and said second shell forcing said second shell to be in a normally closed position such that said second shell constricts the body canal.

38. An implantable apparatus of claim 36 wherein said activating member comprises a housing having at least a first side and a second side whereby the second end of said cable is running slidably through the first side of the housing and is fixed to the second side of the housing such that substantially perpendicular pressure against a portion of said cable between the first side and the second side of the housing results in movement of the first end of said cable against the force exerted by said biasing member causing said second shell to move away from the closed position to allow at least some fluid flow through the body canal.

39. If An implantable apparatus of claim 36 wherein said activating member comprises a stepper motor coupled to said second end of the cable so that activation of the stepper motor causes the second end of said cable to be axially pulled towards the stepper motor resulting in movement of said second shell away from the body canal to allow at least some fluid flow there through.

40. An implantable apparatus of claim 39 farther comprising a magnet for activating the stepper motor.

41. An implantable apparatus of claim 36 wherein said activating member comprises
  a housing having at least a first side and second side whereby the second end of said cable is running slidably through the first side of the housing and is fixed to the second side of the housing; and
  a solenoid such that activation of the solenoid results in downward force being exerted against a portion of said cable between the first side and the second side of the housing thereby causing movement of the first end of said cable against the force exerted by said biasing member causing said second shell to move away from the closed position to allow at least some fluid flow through the body canal.

42. An implantable apparatus of claim 41 further comprising a magnet for activating the solenoid.

* * * * *